United States Patent [19]

Murphy et al.

[11] Patent Number: 5,685,851
[45] Date of Patent: Nov. 11, 1997

[54] IRRIGATION SYRINGE

[75] Inventors: Paul A. Murphy, Grand Rapids; William M. Booth, II, Grand Haven, both of Mich.

[73] Assignee: EAMS Industries, Inc., Grand Rapids, Mich.

[21] Appl. No.: 469,235

[22] Filed: Jun. 6, 1995

[51] Int. Cl.$^6$ ............................................. A61M 37/00
[52] U.S. Cl. ...................... 604/150; 601/155; 601/169; 604/73; 604/183; 604/187; 604/247; 604/275; 604/901
[58] Field of Search ................................ 604/54, 68, 70, 604/71, 73, 93, 118, 131, 151, 150, 181, 183, 187, 257, 245–248, 275, 901; 606/109, 162; 601/154, 155, 159–162, 165, 169

[56] References Cited

U.S. PATENT DOCUMENTS

| | | |
|---|---|---|
| 605,178 | 6/1898 | Guson . |
| 785,524 | 3/1905 | Shea . |
| 1,719,152 | 7/1929 | Watson . |
| 2,112,145 | 3/1938 | Courtney . |
| 2,208,031 | 7/1940 | Hooper . |
| 2,525,419 | 10/1950 | Mellinger et al. . |
| 2,626,524 | 1/1953 | Harman . |
| 2,645,116 | 7/1953 | Baxter . |
| 3,142,297 | 7/1964 | Attebery . |
| 3,669,101 | 6/1972 | Kleiner ............................ 128/66 |
| 3,682,176 | 8/1972 | Kelsen . |
| 3,696,996 | 10/1972 | Lloyd et al. . |
| 3,769,976 | 11/1973 | Victory ............................ 128/229 |
| 3,916,895 | 11/1975 | Davis, Jr. . |
| 3,971,375 | 7/1976 | Hill ................................. 128/173.1 |
| 4,149,315 | 4/1979 | Page, Jr. et al. ..................... 32/22 |
| 4,258,714 | 3/1981 | Leopoldi et al. . |
| 4,413,633 | 11/1983 | Yanda . |
| 4,893,634 | 1/1990 | Kulik et al. . |
| 4,957,483 | 9/1990 | Gonser et al. ...................... 604/30 |

FOREIGN PATENT DOCUMENTS

2063674  6/1981  United Kingdom .

Primary Examiner—Corrine M. McDermott
Assistant Examiner—Cris L. Rodriguez
Attorney, Agent, or Firm—Van Dyke, Gardner, Linn & Burkhart, LLP

[57] ABSTRACT

An irrigation syringe which is particularly adapted for injecting water into a human body cavity, such as for the cleansing of an ear, includes a pressure regulator unit which is connected to, and supported by, a faucet, and a handpiece including a manually operable valve. The regulator unit includes a supply chamber having an inlet which is connected to a pressure water supply such as a faucet, an outlet which supplies pressure regulated water to the handpiece, and a pressure relief outlet having a check valve which opens to allow water to drain, such as into a sink, when the water pressure inside the regulator unit exceeds a predetermined value. A flow limiting orifice at the inlet to the supply chamber helps smooth out pressure fluctuations from the water supply and provides a steady flow from the supply chamber outlet. Temperature and pressure readouts are provided on both the pressure regulator unit and the handpiece.

36 Claims, 7 Drawing Sheets

IRRIGATION SYRINGE

BACKGROUND OF THE INVENTION

This invention relates to a device for injecting water into a human body cavity, such as an ear, to effect cleaning thereof, and more specifically the invention relates to a syringe device which can inject water into a human body cavity continuously as desired.

Those medical professionals who routinely clean patients' ears generally prefer to use irrigation syringe-type devices either alone or possibly in conjunction with curette-type devices. One of the most commonly used category of irrigation syringe-type devices is simple bulb-type devices, which are generally comprised of a flexible bulb having a single opening to which is fitted a nozzle through which water is ingested and discharged. Bulb-type syringes have several disadvantages and are often difficult to use as desired. Because the bulb can only contain a limited, relatively small quantity of water, the device cannot be used continuously for any desired amount of time, and it is often necessary to repeatedly refill the bulb to clean a patient's ear. Another disadvantage with bulb-type syringes is that the pressure of the water exiting the nozzle cannot be easily adjusted and monitored, which in turn can result in discomfort, pain, and possibly injury to the patient if the water is discharged from the nozzle at a pressure which is too high. Water exiting the nozzle opening of a bulb-type syringe at a pressure only slightly in excess of the desired pressure can impinge upon the tympanic membrane at a velocity which can cause considerable pain and even serious injury thereto. Even those bulb-type syringes having flow limiting devices installed within the nozzle or at the juncture between the nozzle and the bulb can eject water at a velocity, which can cause pain and injury upon impact with the tympanic membrane, if the bulb is squeezed with excessive force. Because the bulb must be squeezed by generally applying pressure thereto with the pall and fingers every time the syringe is filled or emptied, repeated use of the device can be fatiguing, aggravating, and even painful.

Another known irrigation syringe includes a pump, connected to a fluid reservoir, and driven by an electric motor. Such devices are capable of pulsatingly or continuously ejecting water from a nozzle opening for a sustained period of time, but do not generally include temperature and pressure indicators for adjusting and monitoring the temperature and pressure of the water issuing from the nozzle. The use of an electric motor also has a number of inherent disadvantages, including increased expense in manufacturing the device and the noise of the motor, which can be annoying and stressful both for the operator and the person whose ear is being cleaned. Additionally, the water in the reservoir must be frequently replaced as it is used.

Fountain-type syringes which are adapted to be connected with a pressure water supply such as at a faucet are not generally used for cleaning ears, because the known devices of this type have not delivered the water to the nozzle opening at the desired pressure and flow rate. More specifically, while some of the fountain-type syringes have included pressure relief valves for limiting the pressure of the water delivered to the nozzle opening, pressure relief valves alone have not adequately provided smooth delivery of water at a relatively constant pressure to the nozzle opening, but have, instead, achieved only a modest, if any, dampening effect of water supply pressure fluctuations, resulting in a pulsating-type flow from the nozzle. Often the rapid opening and closing of the relief valve can itself create a pulsating flow from the nozzle opening. Such pulsations can be annoying to the operator and patient, and can even cause pain or injury to the tympanic membrane, which is sensitive to rapid pressure fluctuations. Additionally, known fountain-type syringes do not include pressure and temperature indicators, which allow adjustment and monitoring of the temperature and pressure of water being delivered to the nozzle opening. The prevailing opinion among physicians is that the ideal temperature for effective ear cleaning is from about 98° F. to about 102° F., because a lower temperature is not as effective for facilitating cleaning and that a higher temperature can cause a patient to experience dizziness and nausea.

Accordingly, a relatively inexpensive, easy to use irrigation syringe capable of continuously discharging water from a nozzle opening for any desired period of time, and capable of delivering water to the nozzle opening at a relatively constant pressure during such period of time, would be highly desirable. Additionally, it would be desirable if such syringe included pressure and temperature indicators, which could be used for adjusting and monitoring the temperature and pressure of water delivered to the nozzle opening. Further, such device should preferably be free of pumps and electric motors to reduce the annoying and stressful noises associated with the operation of pumps and motors.

SUMMARY OF THE INVENTION

The invention provides an irrigation syringe including a pressure regulator unit which can be connected directly to, and supported by, a faucet, and a handpiece which can be gasped between the fingers and palm, and easily manipulated and maneuvered as needed to clean a person's ear. The syringe can discharge water from a nozzle opening at a desirable temperature, pressure, and suitable flow rate continuously for any required amount of time.

In accordance with a first aspect of the invention, the pressure regulator unit includes a supply chamber having a liquid inlet for connecting the supply chamber to a pressurized water supply such as a faucet, and a liquid outlet, which is in fluid communication with an inlet of the handpiece. A flow limiting orifice at the inlet to the supply chamber restricts flow into the supply chamber and generally reduces the pressure of the water supplied from the faucet to provide a relatively smooth and constant flow into the supply chamber, e.g., the orifice tends to smooth out pressure fluctuations from the water supply and provides a more steady flow from the supply chamber outlet. The supply chamber also includes a pressure relief outlet having a check valve, which opens to relieve pressure in the supply chamber when a predetermined pressure is exceeded.

In accordance with another aspect of the invention, the pressure regulator includes a liquid inlet and outlet, a pressure relief outlet, and at least one temperature indicator, which indicates the temperature of water within the syringe. A temperature indicator can be included on the regulator unit to provide feedback as the operator adjusts the valve(s) on the faucet to set the temperature. A temperature indicator can also be placed on the handpiece so that the operator can easily check and monitor the temperature by simply glancing over at the handpiece.

The handpiece is preferably provided with a manually operable valve, which can be opened by merely exerting pressure, such as with a finger or thumb, on a button on the handpiece. Desirably, the valve can be comprised of a spring-loaded clamp, which normally pinches a flexible tube in the handpiece closed to cut off flow, and which allows flow from the nozzle opening when the button on the handpiece is held down.

The regulator unit desirably includes a reservoir chamber, which is in fluid communication with the supply chamber through a flow-restrictive fluid connection such as a pipe or opening connecting the outlet of the supply chamber with the inlet of the reservoir chamber. Water flows from an outlet on the reservoir chamber through a tube to the handpiece. The flow limiting inlet orifice and pressure relief valve of the supply chamber in combination with the flow-restrictive fluid connection between the supply chamber and the reservoir chamber provide an air cushion at the upper portion of the reservoir chamber which achieves additional dampening effect to smooth out pressure fluctuations and pulsations caused by variations in the supply water pressure, rapid periodic discharge of water from the pressure relief outlet in the supply chamber, or both.

Desirably the regulator unit has a pressure indicator, which the operator can use to verify that the syringe is working properly. The handpiece can also be provided with a pressure indicator, which the operator can conveniently monitor while cleaning a person's ear by merely glancing over at the handpiece.

The nozzle on the handpiece is preferably adapted to reversibly receive a disposable, sanitary sheath which promotes proper hygiene. In accordance with a particularly desirable feature of the invention, the handpiece includes a lock which prevents the valve on the handpiece from being pressed, and thereby prevents flow from the nozzle opening, unless a specially adapted sheath is attached to the nozzle. The sheath includes circumferentially spaced lands which provide a gap or vent between the sheath and an ear opening so that excessive hydrostatic pressure does not occur within the ear canal.

These and other features, objects, and benefits of the invention will be recognized by those who practice the invention and by those skilled in the art, from the specification, the claims, and the drawing figures.

DESCRIPTION OF THE PREFERRED EMBODIMENTS

Figure 1:
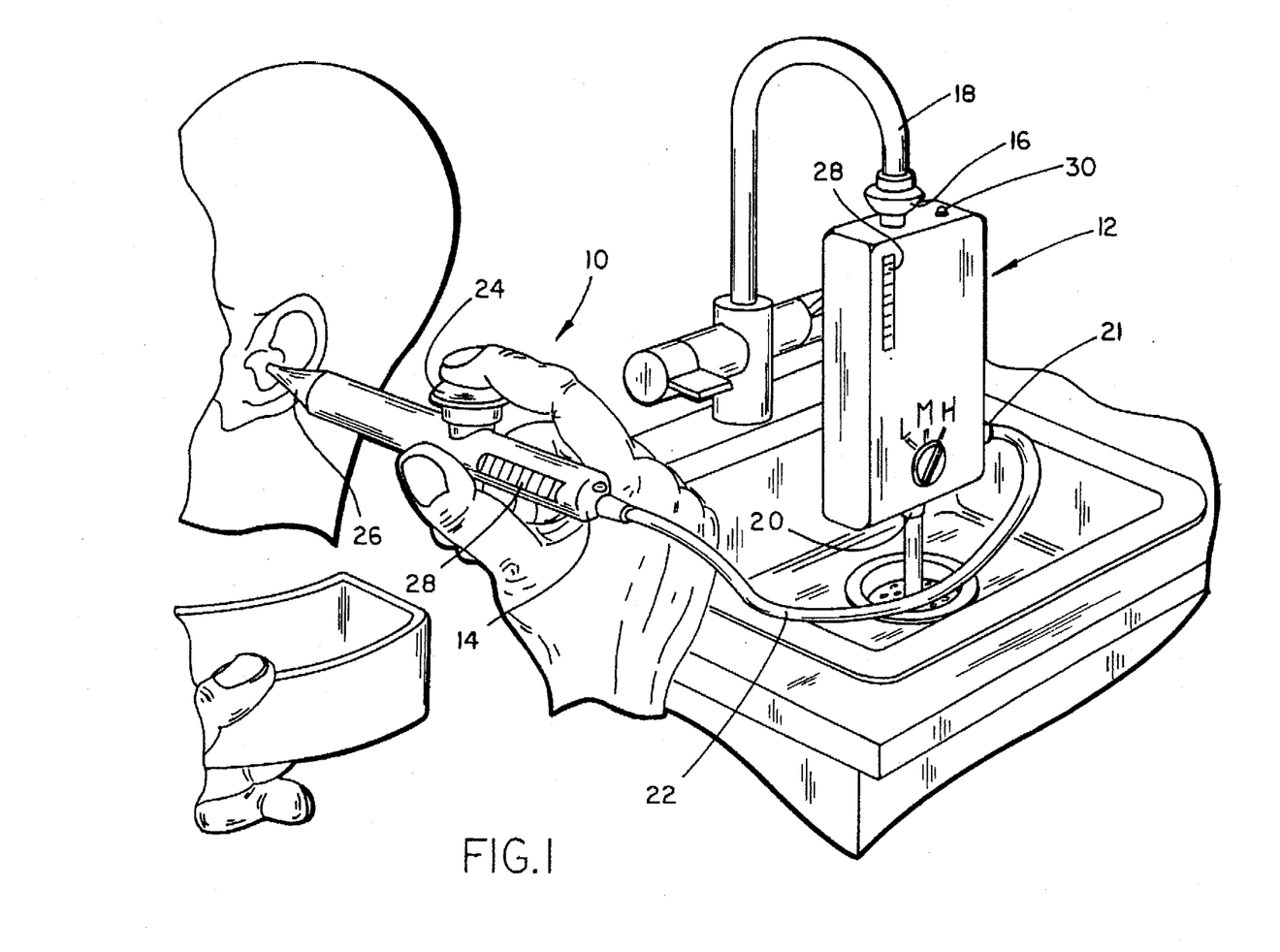
FIG. 1 is a perspective view of an embodiment of the invention showing the syringe being used to clean a person's ear.

In FIG. 1 there is shown a syringe 10 incorporating the present invention which is suitable for cleaning a patient's ear. The syringe 10 includes a pressure regulator unit 12 and a handpiece 14. The pressure regulator unit includes an inlet opening with a quick disconnect coupling 16 connected to a faucet 18. Water is discharged from a pressure relief outlet 20 to maintain the water pressure inside the regulator unit 12 at a prescribed level. Regulated water issues from a supply outlet 21 on the regulator unit 12 and flows through a hose or tube 22 to handpiece 14. A manually operable valve having a pushbutton 24 is provided to control the flow of water from handpiece 14 into an ear which is to be cleaned. The handpiece 14 is adapted to receive a single use, disposable sanitary sheath 26, which snaps onto the injection nozzle end thereof and is retained thereon by a frictional interference fit. A temperature indicator 28 on the regulator unit 12 is provided to monitor the temperature of water issuing from the supply outlet 21 of the regulator unit 12 and flowing to the handpiece. The temperature indicator 28 on the regulator unit 12 is observed during adjustment of the faucet valve(s) to help ensure that water flowing from the injection nozzle of the handpiece 14 is at a safe, desirable temperature, generally in a range from about 98° F. (37° C.) to about 102° F. Regulator unit 12 is also provided with a pressure indicator 30, which can be used during adjustment of the faucet valve(s) to verify that the valve(s) is (are) sufficiently open and that the pressure regulator unit 12 is operating properly. After the faucet valve(s) has (have) been adjusted to deliver water to the handpiece at the desirable temperature and pressure, a medical professional or other operator of the ear syringe 10 grasps the generally cylindrical-shaped handpiece 14 and opens a valve in the handpiece by pressing on button 24 to allow water to flow out from the injection nozzle end of the handpiece for cleaning a person's ear.

Figure 2:
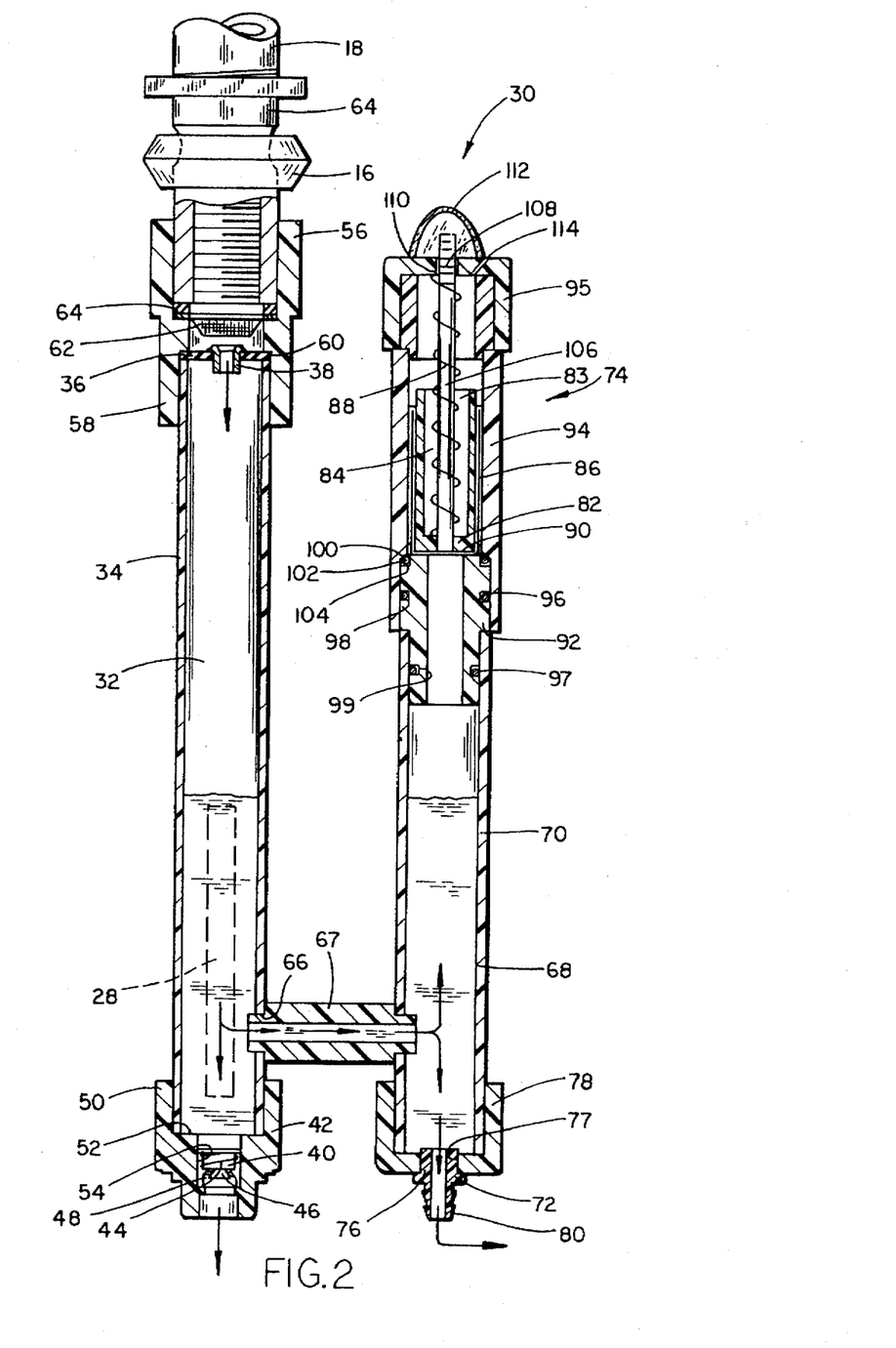
FIG. 2 is an elevational cross-sectional view of one form of the regulator unit.

A pressure regulator unit 12 which employs the principles of the invention is shown in FIG. 2. The regulator unit 12 includes a supply chamber 32 generally defined by a vertically arranged cylindrical tube 34 having at its top end a bulkhead 36 with an opening receiving a flow limiting orifice 38. The bottom end of the cylindrical tube 34 is provided with a check valve 40 fitted within a connector 42. Orifice 38 restricts flow from the faucet into the supply chamber 32 to prevent overloading of check valve 40, to minimize the effects of supply line water pressure variations at the faucet, and to provide a relatively steady flow of water to the handpiece 14 when the valve therein is open. The cross-sectional flow area of the orifice 38 should be less than half, preferably from about two to about ten percent, and more preferably from about five to about ten percent, of the cross-sectional flow area of the check valve when it is fully open. A suitable cross-sectional flow area for the orifice is from about 0.002 to about 0.010 square inches. The flow limiter orifice 38 generally reduces the flow of water into, and limits the flow of water through, the syringe and out from the nozzle opening to a maximum of about one liter every four to five minutes, depending upon the supply pressure of the water. A suitable diameter for orifice 38 is from about 0.025 to about 0.150 inches, and more preferably from about 0.05 to about 0.10 inches.

Check valve 40 is a poppet-type valve which remains closed below a preselected pressure differential and opens above the preselected pressure differential, whereby the check valve 40 acts as a pressure regulator. Suitable zero leakage, positive sealing, low inertia poppet design cartridge check valves are commercially available, e.g., model number 110 from Smart Products, Inc., 2365 Paragon Drive, Unit H, San Jose, Calif. 95131. Such valves are provided with a spring 44 which urges plunger 46 to seat against an O-ring 48, unless a predetermined pressure differential is exceeded which causes the spring to compress and the plunger to move downwardly and become unseated from the O-ring to allow water to flow outwardly from supply chamber 32. Spring 44 can be selected to allow the valve 40 to open at generally any desired pressure in the range from about 0.2 to about 15 psi. However, to provide the desired cleansing action without risking pain or injury to the person whose ear is being cleaned, the check valve is preferably selected or designed to have an opening or cracking pressure of from about 1.0 to about 3.5 psi.

The illustrated connector 42 is a generally cup-shaped fitting having an upstanding cylindrical section 50, which overlaps the end of cylindrical tube 34, an internal circumferential shoulder 52 against which the bottom edge of cylindrical tube 34 generally abuts, and an axial bore or opening 54 in which check valve 40 is fitted. The connector 42 is sealingly secured to the lower end of tube 34 with a suitable cement or adhesive.

The upper end of the tube 34 includes a female quick disconnect coupling 16 threadably received in an adaptor 56, which is sealingly secured to the top end of tube 34 with a suitable cement or adhesive. Adaptor 56 has a lower cylinder portion 58 which overlaps the top end of tube 34, and an inner rim 60 which abuts the top edge of tube 34. A metal or plastic screen 62 is supported along its circumferential edges on an internal shoulder 64 of adaptor 56 and is captured between the shoulder 64 and the lower edges of female quick disconnect coupling 16. Screen 62 catches sediment and other solid materials to prevent such materials from plugging orifice 38 or entering the ear. The female quick disconnect coupling 16 snaps onto a male quick disconnect coupling 64, which is threadably connectable to a faucet 18. Quick disconnect couplings, also known as snap fittings, are commercial available such as from Chicago Specialty, 377 Woodland Avenue, Elyria, Ohio 44036.

A lateral discharge outlet 66 is provided near the bottom end of tube 34 to supply pressure regulated water to handpiece 14. While regulated water can be supplied directly from discharge outlet 66 to handpiece 14 via tubing, the outlet 66 is preferably in fluid communication, via a connecting pipe 67, with a reservoir chamber 68, which is generally defined by a second cylindrical tube 70. Tube 70 has a bottom supply outlet 72 through which pressure regulated water is supplied to handpiece 14 via tube 22, and a pressure indicator 30, which is sealingly secured to the top of tube 70. Pipe 67 has a cross-sectional flow area, which is preferably less than the cross-sectional flow area of open check valve 40. The flow limiting inlet orifice 38 and pressure relief check valve 40 of supply chamber 32 and flow restrictive connecting pipe 67 serve to provide an air cushion which is trapped at the upper portion of the reservoir chamber and acts as a buffer to pressure fluctuations in the water supplied by faucet 18 and pressure fluctuations caused by discharge of water through check valve 40, thereby providing more uniform pressure to the handpiece 14. Outlet 72 is comprised of a fitting having a cylindrical portion 76 secured, as with a suitable cement or adhesive, within a circular bore or opening 77 of a cap-type member 78, and an outward downwardly projecting barbed end 80 which is adapted to be received within, and frictionally engage the inner walls at the end of a flexible tube 22. Cap-type member 78 has an upstanding cylindrical portion which overlaps walls at the bottom of cylindrical tube 70; and is secured thereto such as with a suitable cement or adhesive.

Pressure indicator 30 is relatively simple, inexpensive, and can provide either a qualitative or, if desired, a quantitative indication of the pressure inside reservoir chamber 68. Pressure indicator 30 is comprised of a hollow, cylindrical piston 82 which has an open end 83 extending upwardly and is movable within a cylindrical volume 84 separated from the reservoir chamber 68 by a rolling diaphragm 86. Diaphragm 86 is an elastic, fluid-impermeable, balloon-like rubber or flexible synthetic component, the edges of which are continuously sealingly retained at the lower edges of the internal walls of the cylindrical volume 84. A compression spring 88 urges piston 82 downward toward reservoir chamber 68 against stop shoulders 90 of a connector 92 which sealingly connects cylindrical tube 70 with internally tapered cylindrical tube 94. The top end of compression spring 88 engages the underside of a cap 95, which is secured to the top end of tube 94 such as with a suitable cement or adhesive, while the bottom end of spring 88 extends through upper, open end 83 of piston 82 and engages a generally upwardly facing surface of the piston. Sealing engagement between connector 92 and tubes 70 and 94 is maintained with compressible O-rings 96 and 97 located generally within circumferential grooves 98 and 99 of connector 92.

As illustrated in FIG. 2, the edges at the opening of the balloon-like diaphragm 86 are continuously sealingly secured at the internally tapered section 100 of tube 94 by wedging the edges of diaphragm 86 and an overlying compressible O-ring 102 between a circumferential groove 104 at the top outer edge of connector 92 and the tapered section 100. The open edges of diaphragm 86 are preferably rolled up to form compressible O-ring-like portion 102. Attached to the piston 82 is a upstanding rod 106 receiving spring 88 telescoped therearound and having calibration marks 108 at its top end which indicate the pressure within the reservoir chamber 68. The rod 106 passes generally through the helical axis of compression spring 88 and helps properly position the spring 88 so that the helical axis thereof is generally parallel with the longitudinal axis of the piston and cylindrical volume 84. The top end of the rod 106, which bears calibration marks 108, passes through an opening 110 in the top of cap 95. Rod 106 extends further upwardly through opening 110 as the pressure differential between the reservoir chamber 68 and the volume 84 above the diaphragm 86 increases. A clear, generally dome-shaped lens 112 positioned over opening 110 can be provided with a sight line which can be visually aligned with one of the calibration marks 108 on the rod 106 to provide a pressure reading. The calibration marks can be qualitative (e.g., low, medium, and high) as shown in FIG. 2 or quantitative (e.g., in units of pressure such as psi) if desired. The cap 95 includes a vent 114, which provides fluid communication between the volume 84 and the ambient atmosphere to ensure that the reading provided by pressure indicator 30 is gauge pressure, i.e. pressure above ambient atmospheric pressure.

Reference numeral 28 designates a temperature indicator attached to the exterior surface of the pressure regulator unit 12, which is used to measure the temperature of water passing therethrough and to handpiece 14. Various temperature indicating devices can be used, including thermometers, thermocouples, or the like. Preferably, temperature indicator 28 is of the type comprising a thin strip encapsulating liquid crystals which change color when the temperature changes. Such temperature indicators are relatively inexpensive and commercially available. A preferred temperature indicator, available from Cole-Parmer Instrument Company, Niles, Ill. 60714, is designated "Cat. no. G-90306-08."

Handpiece 14 (shown in FIGS. 3A and 3B) includes a generally tubular housing 118 adapted to be hand-held, and which includes a fluid inlet 120 in fluid communication with outlet 72 of the pressure regulator unit 12, and a manually operable valve 122 for controlling the flow of water from a water injection nozzle 124. Preferably, handpiece 14 also includes a temperature indicator 126 (which is preferably similar or substantially identical to temperature indicator 28 on regulator unit 12) and a pressure indicator 128 to facilitate convenient monitoring of the temperature and pressure of water being discharged from the handpiece 14 without needing to divert attention to the regulator unit 12. For convenience in maintaining proper hygienic conditions, the handpiece 14 is preferably adapted to receive a disposable sanitary sheath 26 which easily snaps onto and off of the fluid injection nozzle end of the handpiece. Sheath 26 includes a plurality of fin-like projections or lands 119 which are uniformly spaced circumferentially about the exterior surface of the sheath. The space between adjacent lands 119 serve as vents to allow water to escape from the ear when the nozzle is inserted into an ear, thereby providing a safety feature which prevents excessive hydrostatic pressures from building up in the aural canal.

Figure 3A:
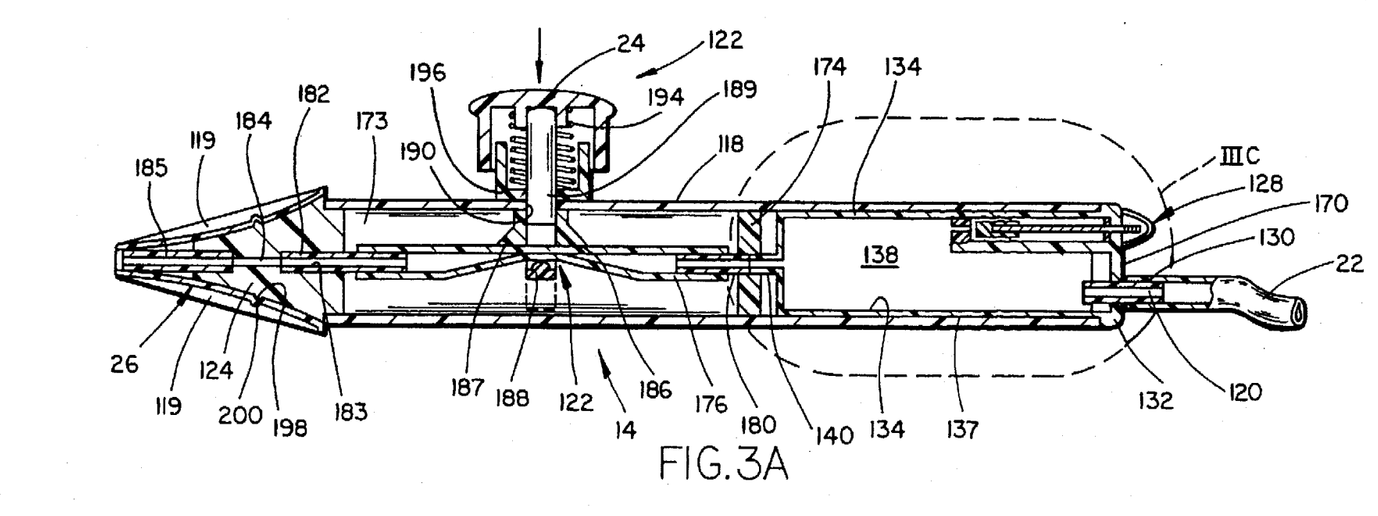
FIG. 3A is a sectional side elevation of a handpiece which can be used with any of the regulator units desired herein.
Figure 3B:
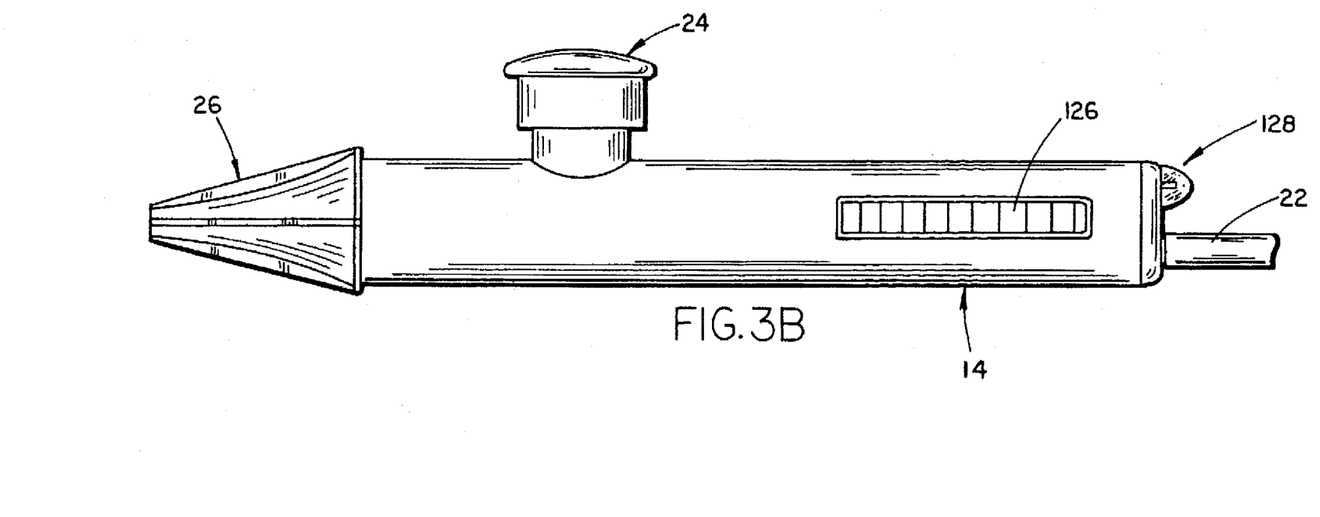
FIG. 3B is a side elevation of the handpiece of FIG. 3A.
Figure 3C:
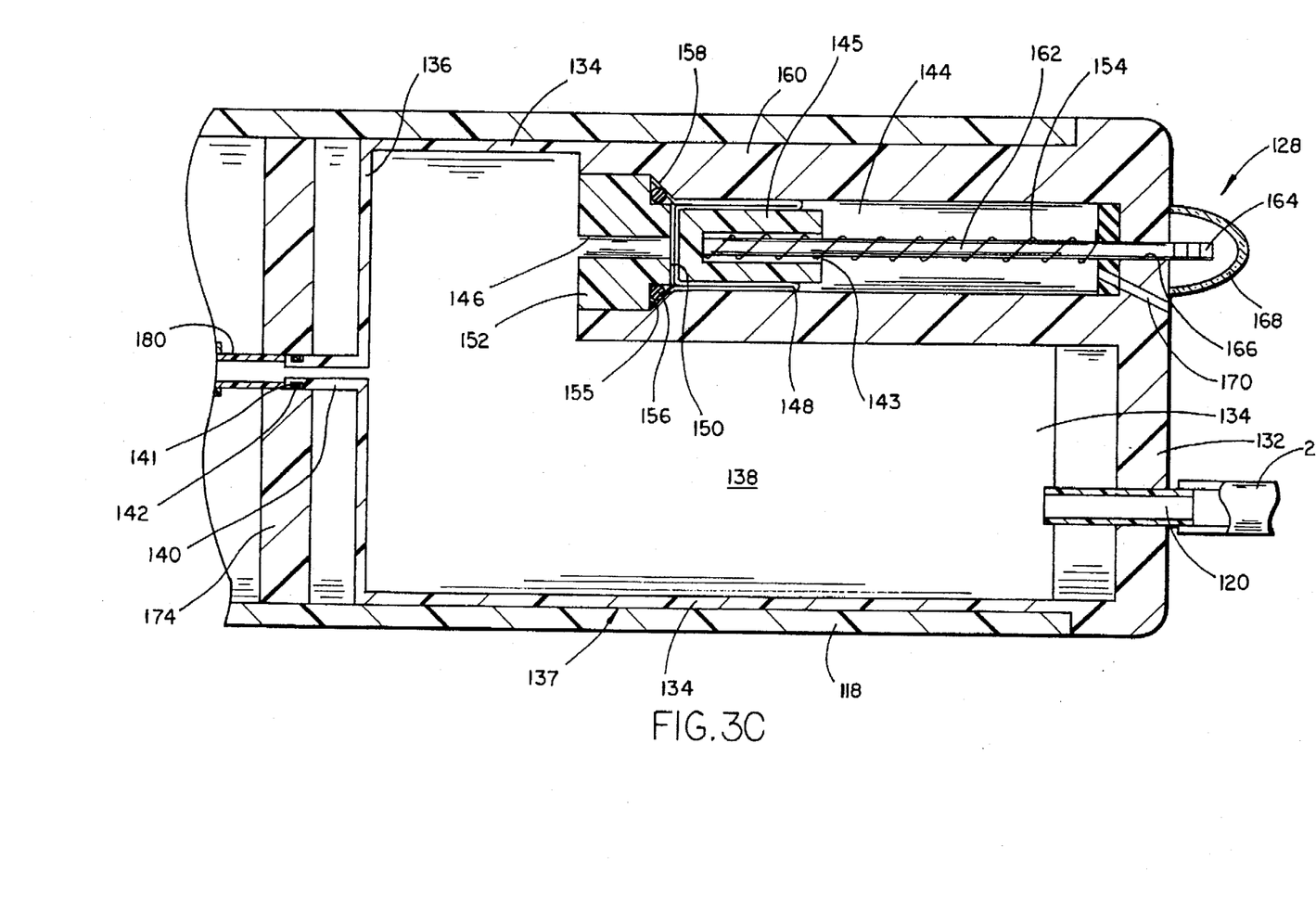
FIG. 3C is an enlarged, fragmentary, sectional side elevation of area IIIC of the handpiece shown in FIG. 3A.

The fluid inlet 120 to handpiece 14 is a tube coupling which passes through and is secured in an opening or bore 130 through an endcap 132, which is attached at an inlet end of housing 118. The outwardly projecting end of tube coupling 120 is received within an end of a flexible tube 22 through which water flows from the regulator unit 12 into handpiece 14. In accordance with a preferred aspect of the invention, endcap 132, cylinder walls 134, and internal end wall 136 together define an information-water supply module 137 having a water tight fluid chamber 138. The module 137 includes, in addition to inlet 120, an outlet tube 140 having a circumferential groove 141 in which is received an O-ring 142. Outlet tube 140 is inserted into an opening through bulkhead 174 with O-ring 142 providing a water tight seal between outlet 140 and tube connector 180. The module 137 is designed so that it can be easily withdrawn from the handpiece 14 and replaced with another similar module in the event that the pressure indicator 128 or temperature indicator 126 should become worn or damaged. More specifically, module 137 has a cylindrical or barrel shape which slides into a cylindrical recess of the handpiece which is generally defined by wall 118 and bulkhead 174. The module 137 is preferably snap-fit into the end of the handpiece 14, and includes appropriate detents or the like which can be engage by conforming recesses on the walls 118.

Pressure indicator 128 is generally similar to pressure indicator 30 of the regulator unit 12. More specifically, pressure indicator 128 includes a cylindrical piston 145 which is open at one end 143 and is movable in a cylindrical volume 144 within a tube 160. Volume 144 is separated from pressurized water which enters an inlet opening 146 by a rolling diaphragm 148, generally similar to diaphragm 86. Piston 145 is urged against a shoulder 150 of a stop member 152 by a compression spring 154, the ends of which bear against opposing surfaces of endcap 132 and piston 145. Stop member 152 has a circumferential groove 155 at one end for receiving a compressible O-ring 156. The edges at the opening of balloon-like diaphragm 148 are continuously sealingly secured by wedging the edges of diaphragm 148 and overlying O-ring 156 between groove 155 and a tapered section 158 of tube 160 which generally defines volume 144. Rod 162 having calibration marks 164 is attached to piston 145, and projects through the helical axis of spring 154 and through an opening or bore 166 in endcap 132. The calibration marks 164 can be seen through a clear, generally dome-shaped lens 168 positioned over opening 166. A vent 170 in endcap 132 provides communication between the volume 144 and the ambient atmosphere to provide a gauge pressure reading (i.e., pressure above ambient atmospheric pressure) of the pressure regulated fluid in the handpiece 14. Pressure indicator 128 can be supported within handpiece 14 by securing tube 160 to an interior surface of housing 118 and/or an interior surface of endcap 132. Any suitable means such as cement or adhesive can be used to secure tube 160 to housing 118 and endcap 132.

Figure 4A:
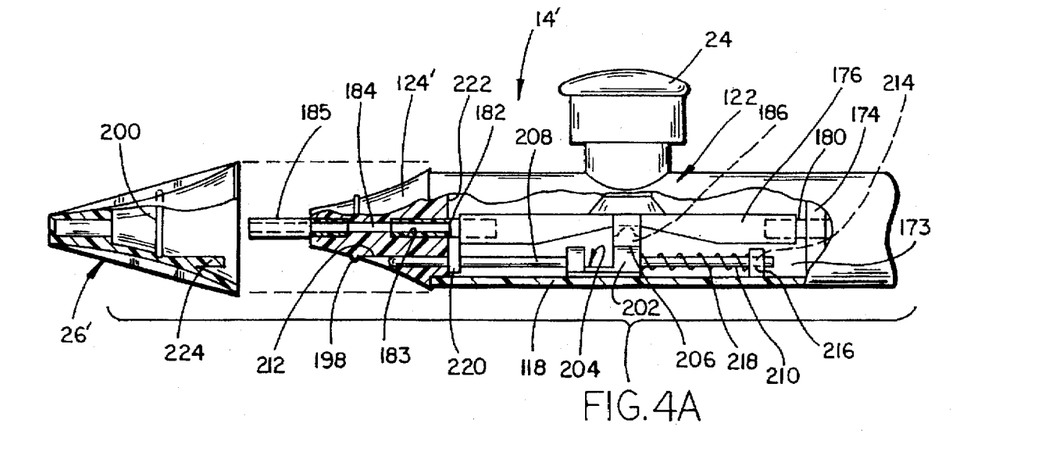
FIG. 4A is a fragmentary, sectional side elevation view of an alternative handpiece having a locking mechanism which prevents use of the unless a protective sheath (not shown) is mounted on the nozzle.

A pinch-type valve 122 (FIGS. 3A, 4A and 4B) is disposed at a valve section 173 of handpiece 14, which is generally delimited by a bulkhead 174 which is situated intermediate the ends of the handpiece, and a nozzle 124 which is positioned at the end of the handpiece opposite to inlet 120. When valve 122 is open, regulated water flows from the regulator unit 12 into handpiece 14 through tube 22, inlet tube coupling 120, fluid chamber 138, rigid tube connector 180 passing through and secured within a bore through bulkhead 174, flexible tube 176, rigid tube connector 182 secured at one end of an axial cylindrical bore 183 through nozzle 124, a reduced diameter section 184 of the bore 183, and through and outward from an open end of a rigid tubular nozzle tip 185.

Valve 122 (FIG. 3A) includes upper bearings 186, 187 and a lower movable bearing 188 having a rounded upwardly projecting protuberance which normally forcibly pushes up against the lower surface of flexible tube 176 causing it to pinch closed, as shown in FIG. 3(A). Bearing 186 is an integral part of stem 189 which passes between fixed bearings 186, 187 and extends outwardly through aperture 190 in the side of housing 118. The outward end of stem 189 is attached to the underside of a pushbutton 24. A spring 194 has ends which bear against the underside of button 24 and the recessed bottom of cup-shaped spring retainer 196 to urge button 24 upwardly as shown in FIG. 3(A). Button 24 is pressed such as with a thumb or finger to lower bearing 188 downwardly to the position A (indicated by dotted lines). Due to the resiliency of tubing 179, this allows the flexible tube 176 to flex, expand, and return to a normal cylindrical shape B (indicated by dotted lines) which causes water to flow freely therethrough and from the nozzle end of the handpiece 14.

Nozzle 124 includes a circumferential rib 198, which engages a circumferential groove 200 on the interior wall of a disposable generally cone-shaped safety sheath 26. Hence, sheath 26 can be snapped on and off of nozzle end 176.

Figure 4B:
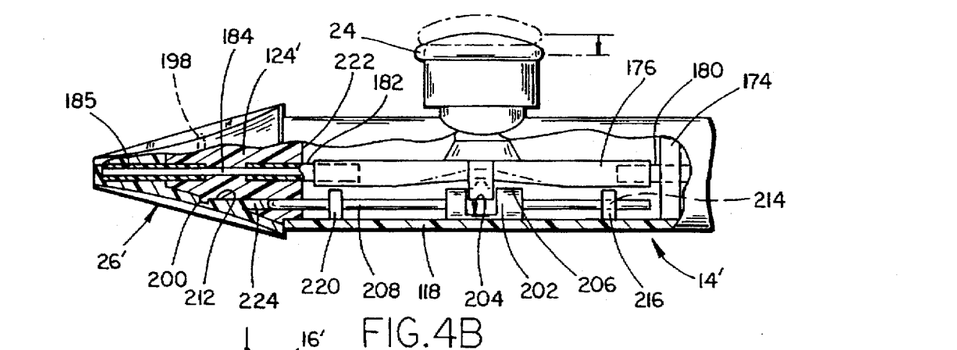
FIG. 4B is a fragmentary, sectional side elevation of the handpiece shown in FIG. 4A, with a sheath mounted on the nozzle thereof.

In accordance with a further preferred aspect of the invention, alternate handpiece 14' (FIGS. 4a and 4b) is provided with a spring-loaded valve lock 202 which prevents button 24 from being pressed downwardly to unpinch tube 176 and allow water to flow therethrough unless a specially adapted sheath 26' (FIGS. 4A and 4B) is secured to nozzle 124'. This feature will generally prevent use of handpiece 14' unless sheath 26' is secured thereto. Because sheath 26' will typically be removed and disposed of after a single use, valve lock 202 helps promote proper hygiene. Lock 202 slides along the inner wall of housing 118 from a first position (FIG. 4B) wherein a recess 204 is aligned with bearing 188 to allow button 24 to be freely pressed and released as desired, to a second position (FIG. 4A) wherein a raised land portion 206 adjacent to the recess 204 acts as a stop which prevents bearing 188 from being moved downwardly to allow flow through tube 176 and out of handpiece 14'. Lock 202 is guided between the locked position (FIG. 4B) and the unlocked position (FIG. 4A) by shafts 208 and 210 which are attached to opposite sides of lock 202 and maintained in substantially axial alignment by circular bore 212 through nozzle 124' and circular bore 214 through wall 216 which is fixed to the interior wall of housing 118. When sheath 26' is removed from nozzle 124' with button 24 released, a spring 218 urges lock 202 toward nozzle 124' until a stop ring 220 affixed to shaft 208 engages interior transverse wall 222 of nozzle 124', and raised portion 206 of lock 202 is disposed beneath bearing 188 to prevent downward movement thereof. Spring 218 is positioned on shaft 210 with its helical axis generally coincident with the longitudinal axis of shaft 210, and with the ends of spring 218 engaging wall 216 and lock 202 to urge lock 202 to the left and away from wall 216 as shown in FIG. 4B. Sheath 26' includes a cylindrical stub 224 projecting from the inner wall thereof. When sheath 26' is properly attached to nozzle 124', stub 224 slides into bore 212 and engages the end of shaft 208 and forces it, along with lock 202, to move toward the water inlet side of handpiece 14 against the force of spring 218 until recess 204 is directly beneath bearing 188 so that it can be moved downwardly unimpeded by lock 202. To facilitate a snap-type attachment of sheath 26' to nozzle 124', nozzle 124' includes a circumferential rib 198 which engages a circumferential groove 200 on the interior wall of sheath 26'.

Figure 5A:
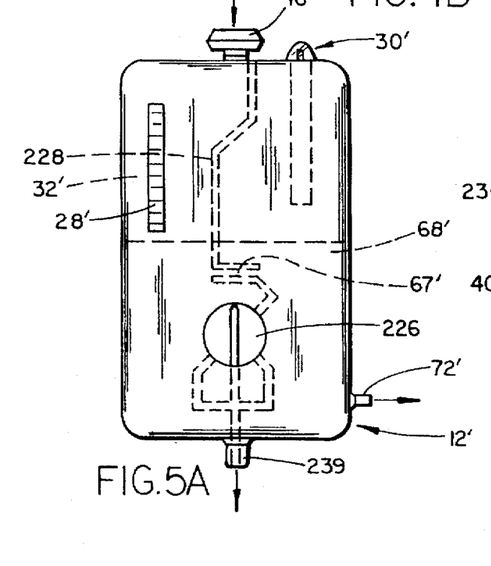
FIG. 5A is a front elevational view of a preferred regulator unit having a supply chamber and a reservoir chamber integrally formed together.

In accordance with another embodiment of the invention, a regulator unit 12' (FIGS. 5a and 5b) can be provided with supply chamber 32' and reservoir chamber 68' integrally formed together such from a polymeric thermoplastic using an injection molding process. Regulator unit 12', except for its shape and a plurality of check valves 40a, 40b, 40c (FIG. 5B) and an associated check valve selector 226 (described hereinafter), is generally similar to regulator unit 12. Regulator unit 12' is generally box-shaped and includes a partition 228 which divides the interior thereof into supply chamber 32' and reservoir chamber 68', which are in fluid communication via an integrally formed flow restrictive, tubular passageway 67'. Regulator unit 12' also includes a quick disconnect coupling 16', a sediment screen (not shown), a flow limiting orifice (not shown), a temperature indicator 28', a pressure indicator 30', and an outlet 72', all of which are similar or substantially identical to the corresponding parts of regulator unit 12.

Figure 5B:
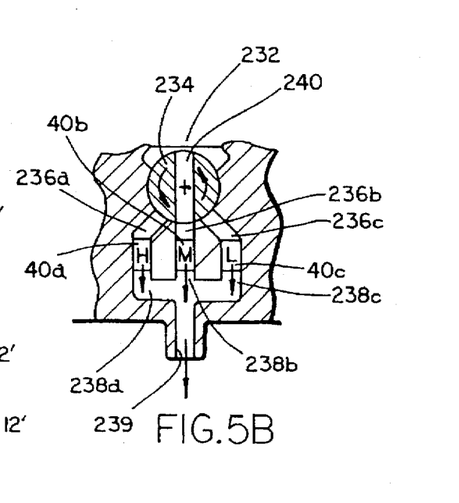
FIG. 5B is a sectional front elevation of the alternative regulator shown in FIG. 5A.

Regulator unit 12' is also provided with a plurality of check valves 40a, 40b, and 40c, each of which has a different opening or cracking pressure, and a pressure selector 226. The pressure selector has a pressure relief inlet 232 in fluid communication with supply chamber 32' and a flow selector valve 234. Check valves 40a, 40b, 40c each have an inlet 236a, 236b, 236c, respectively, and an outlet 238a, 238b, 238c in fluid communication with the ambient atmosphere via pressure relief outlet 239. Valve 234 has a fluid passageway 240 which is movable to alternately provide fluid communication between pressure relief opening 232 and one of the inlets 236a, 236b, 236c. The cracking pressures for valves 40a, 40b, 40c can be, for example, selected to provide a low water pressure to handpiece 14 such as about 1.0 to out 1.5 psi, a medium pressure such as from about 1.5 to about 2.5 psi, and a high pressure such a from about 2.5 to about 3.5 psi. This allows the operator to choose a higher water discharge pressure to provide better cleaning action or to choose a lower water discharge pressure to reduce discomfort to an individual whose ear is being cleaned, should that individual exhibit sensitivity to the water being discharged into the ear. A flow limiting orifice at the inlet of reservoir chamber 32' in combination with valves 40a, 40b, 40c and flow restrictive tubular passageway 67' serve to provide an air cushion which is trapped at the upper portion of the reservoir chamber and acts as a buffer to pressure fluctuations, whereby water is delivered to the handpiece 14 at a more uniform pressure.

Ear syringe 10 is prepared for use by connecting the inlet opening of the regulator unit (either 12 or 12') to a faucet 18, preferably using quick disconnect couplings 16 or 16' and 64, selecting the desired pressure if regulator unit 12' is being used, adjusting the faucet valve(s) while observing the temperature indicator 28 and pressure indicator 30 until adequate pressure and temperature is achieved. After the syringe 10 has been prepared for use, the operator attaches a new, sanitary sheath 26 or 26' to the nozzle, merely grasps the handpiece 14 in one hand and, using a finger or thumb on that hand, depresses button 24 to cause water to issue from the nozzle end of the handpiece. The operator can easily monitor temperature and pressure of water issuing from handpiece 14 by occasionally glancing at the temperature indicator 126 and pressure indicator 128 on handpiece 14.

A further alternative embodiment of the invention is shown in FIGS. 6A, 6B, 6C, and 6D. The regulator unit 300 incudes a pair of concentric cylindrical tubes, including an outer rigid tube 302 which partially defines the housing for regulator unit 300, and an inner rigid tube 304 (FIG. 6C) which, together with a base 306 and a top member 308, define a supply chamber 310 and a reservoir chamber 312.

Figure 6A:
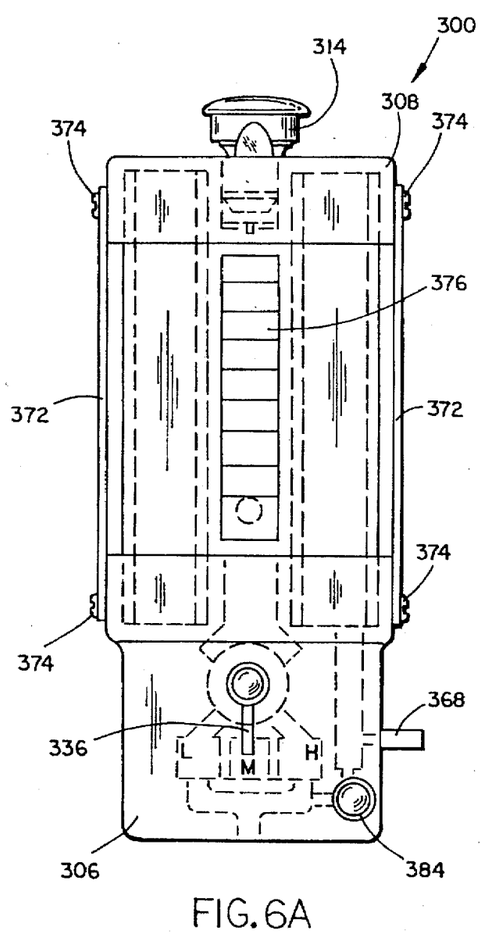
FIG. 6A is a front elevational view of a further embodiment of a regulator unit for the invention, employing concentric cylindrical tubes, the volume defined by the inner tube defining a supply chamber, and the annular space between the tubes defining a reservoir chamber.
Figure 6B:
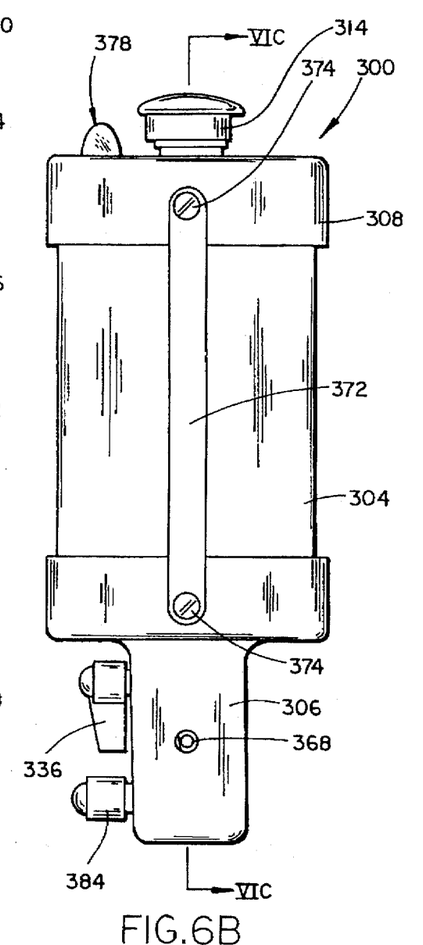
FIG. 6B is a side elevational view of the regulator unit shown in FIG. 6A.

Regulator unit 300 includes a female quick disconnect coupling 314 adapted to be quickly connected to and disconnected from a male quick disconnect coupling 316 which is connected to a faucet 318.

The unit 300 also includes a rotatable pressure selector valve 320 having a fluid passageway 322 which provides fluid communication between the supply chamber 310 and one of a plurality of inlet passageways 324, 326, 328 to check valves 330, 332, 334 respectively, which are poppet-type valves having different crack or opening pressures. The selector valve 320 is operatively connected to a knob 336 which is rotated to align passageway 322 with one of the inlet passageways 324, 326, 328 depending on the desired pressure of the water which is to issue from a handpiece 14 (such as shown in FIGS. 1, 3A, 3B, 4A, 4B). Once a position for the selector knob 336 has been chosen, the associated check valve 330, 332, 334 will open if the pressure inside supply chamber 310 exceeds a predetermined level allowing water to drain from the unit through common drain opening 338, which is in fluid communication with the outlet side of the check valves via outlet passageways 340, 342, 344.

Figure 6C:
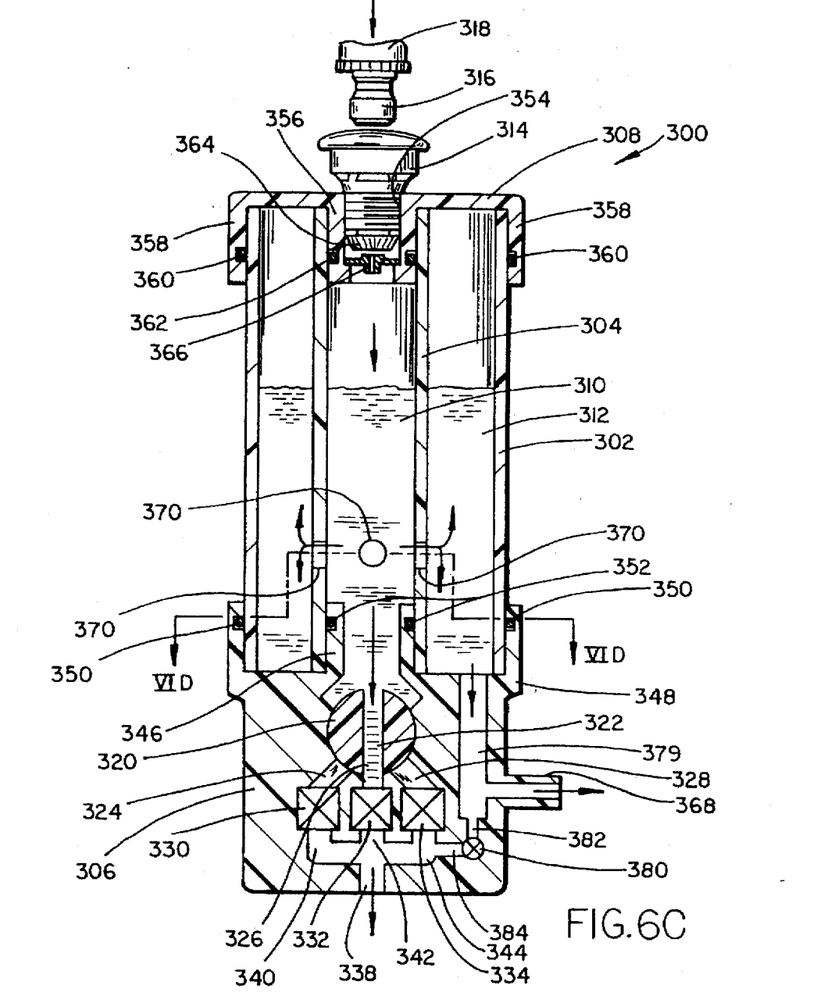
FIG. 6C is a sectional front elevation of the regulator unit as viewed along lines VIC—VIC of FIG. 6B.

The base 306 includes concentric circular support walls 346, 348 which support and sealingly engage the interior walls of inner rigid tube 304, and the exterior walls of outer rigid tube 302, respectively. Tubes 302, 304 are secured to walls 348, 346, respectively, by a frictional or interference-type fit. O-ring seal 350 provides a fluid tight seal between the interior side of wall 348 and the exterior side of rigid tube 302. O-ring seal 352 provides a fluid tight seal between the exterior side of wall 352 and the interior side of tube 304.

The top member 308 is a cap-like member having central threaded inlet opening 354 for securely receiving female quick connect coupling 314, an inner circular wall 356, the outer side of which engages the interior side of inner rigid tube 304, and a depending skirt flange 358 the interior side of which engages the exterior side of tube 302. Tubes 302, 304 are secured to walls 358, 356, respectively, by a frictional or interference-type fit. O-ring seal 360 provides a fluid tight seal between the interior side of flange 358 and the exterior side of tube 302. O-ring seal 362 provides a fluid tight seal between the exterior side of wall 356 and the interior side of tube 304. Positioned within the inlet opening 354 is a sediment screen 364, for screening particulate matter which could cause injury if propelled toward the tympanic membrane, and a flow limiting orifice 366 which helps control flow through the unit 300 and to the handpiece 14 from outlet 368, and helps smooth out or dampen pressure and flow fluctuations from the faucet supply. A plurality of flow restrictive openings 370 in tube 304 allow water to flow into the annular reservoir chamber 312 between inner and outer tubes 304, 302. The openings 370 are preferably sized so as to provide a flow restriction which helps further smooth out or dampen any flow or pressure fluctuations from the faucet. As with the previously described embodiments, flow limiting orifice 366, valves 330, 332, 334, and flow restrictive openings 370 cooperate to provide an air cushion which is trapped at the upper portion of reservoir chamber 312 and which serves as a buffer to pressure fluctuation to provide a smoother flow of water to the handpiece.

The top member 308, inner and outer tubes 302, 304 and base 306 are securely held together by a pair of side bars 372, each of which is secured, as with a fastener 374, at one end to the base 306 and at the other end to the top member 308.

The regulator unit 300 includes a temperature indicator 376, and a pressure indicator 378, which are substantially identical to temperature indicators 28, 28', and pressure indicators 128, 30', respectively, of the previous embodiments.

Figure 6D:
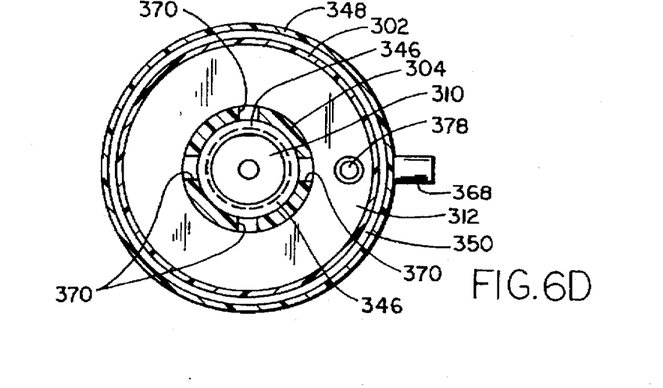
FIG. 6D is a sectional plan view of the regulator unit as viewed along lines VID—VID of FIG. 6C.

Regulator unit 300 includes a vertical bore 379 in the base which provides fluid communication between the reservoir chamber 312 and the outlet 368. A valve 380 is also provided in the base with fluid passageway 382 connecting bore 379 with one side of valve 380 and passageway 384 connecting the other side of the valve 380 with the passageway 328 and drain opening 338. A knob 384 is operatively connected to valve 380 which can be opened to allow liquid to drain from the regulator unit 300 after use.

To use regulator unit 300, inlet opening 354 is first connected to a water supply, such as by connecting female quick disconnect coupling 314 to a male quick disconnect coupling 316 threaded onto a faucet 318. The desired pressure selection is then made by turning knob 336 to the appropriate position. For example, valves 330, 332, and 334 could be selected so that the supply pressure of water delivered to the hand unit can be about ½, 1, or 1½ psig, as desired, depending on which valve is selected. Next, the valve 380 should be closed by appropriate rotation of knob 384. A handpiece (such as handpiece 14 shown in FIG. 3A) is then connected to the outlet 368 through a flexible tube. The valve(s) for faucet 318 is (are) then turned on and adjusted to achieve the desired temperature. After the desired temperature is achieved, the handpiece can then be used to clear a person's ear by pressing on button 24 to allow water to issue from nozzle tip 185.

It will be understood by those who practice the invention and by those skilled in the art, that various modifications and improvements may be made to the invention without departing from the spirit of the disclosed concept. The scope of protection afforded is to be determined by the claims and by the breadth of interpretation allowed by law.

The embodiments of the invention in which an exclusive property or privilege is claimed are defined as follows:

1. An irrigation syringe, comprising:
   a handpiece;
   a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice opening to said supply chamber, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;
   said check valve having a first flow area, said flow limiting orifice having a second flow area which is less than said first flow area of said check valve to prevent overloading of said check valve when liquid flows into said supply chamber through said flow limiting orifice such that said pressure regulator unit provides a generally steady flow of pressure regulated liquid from said liquid outlet to said handpiece,
   said handpiece having a liquid inlet in fluid communication with said liquid outlet of said pressure regulator unit, and a discharge opening from which pressure regulated liquid from said liquid inlet of said handpiece issues.

2. The syringe of claim 1, wherein said handpiece further includes a manually operable valve in fluid communication with said liquid inlet of said handpiece and said discharge opening of said handpiece for controlling the flow of liquid from said discharge opening.

3. The syringe of claim 1, wherein said handpiece further includes a temperature indicator mounted on said handpiece for indicating the temperature of liquid in said handpiece.

4. The syringe of claim 1 wherein said second flow area of said flow limiting orifice is less than one-half of said first flow area of said check valve.

5. The syringe of claim 1, wherein said liquid inlet of said supply chamber includes a quick disconnect coupling for facilitating rapid connection of said liquid inlet to a faucet and rapid disconnection of said liquid inlet from a faucet.

6. An irrigation syringe, comprising:
   a handpiece;
   a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, a discharge opening from which pressure regulated liquid from said liquid inlet of said handpiece issues, and a manually operable valve in fluid communication with said liquid inlet and said discharge opening of said handpiece for controlling the flow of liquid from said discharge opening, said manually operable valve comprising a flexible tube which constitutes at least a portion of the flow path between said liquid inlet of said handpiece and said discharge opening of said handpiece, and a plurality of bearings which cooperate to engage said flexible tube to reduce the cross-sectional flow area thereof and restrict flow therethrough, at least one of said bearings being movable away from said flexible tube to allow the same to flex and assume a large cross-sectional flow area.

7. The syringe of claim 6, wherein said handpiece includes a nozzle and a disposable sheath removably mounted thereon.

8. The syringe of claim 7, wherein said handpiece includes a releasable lock which prevents said manually operable valve of said handpiece from being opened unless said sheath is attached to said nozzle.

9. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues, said pressure regulator unit further including a reservoir chamber in fluid communication with said supply chamber, and a flow restrictive fluid connection providing said fluid communication between said supply and said reservoir chambers.

10. The syringe of claim 9, wherein said flow-restrictive fluid connection includes a pipe and a partition separating said supply and reservoir chambers.

11. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues, said pressure regulator unit further including a temperature indicator mounted thereon for indicating the temperature of liquid in said pressure regulator unit.

12. The syringe of claim 11, wherein said pressure regulator unit further includes a pressure indicator mounted thereon for indicating the pressure of liquid in said pressure regulator unit.

13. The syringe of claim 12, wherein said pressure indicator includes a cylinder and a spring-loaded piston movable within said cylinder in response to a change in pressure in said pressure regulator unit, said cylinder being separated from said liquid contained in said pressure regulator unit by an elastic, fluid-impermeable diaphragm, the pressure in said pressure regulator unit being indicated by the position of said spring-loaded piston in said cylinder.

14. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues, said pressure regulator unit further including a pressure indicator mounted thereon for indicating the pressure of liquid in said pressure regulator unit.

15. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, a discharge opening from which pressure regulated liquid from said liquid inlet of said handpiece issues, and a temperature indicator mounted on said handpiece for indicating the temperature of liquid in said handpiece, said handpiece further including a pressure indicator mounted thereon for indicating the liquid pressure in said handpiece.

16. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, a discharge opening from which pressure regulated liquid from said liquid inlet of said handpiece issues, and a pressure indicator mounted on said handpiece for indicating the pressure of liquid in said handpiece.

17. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues;

said pressure relief outlet including a plurality of check valves, each check valve having an inlet side and an outlet side, said outlet side of each of said check valves being in communication with the ambient atmosphere, each check valve having a predetermined opening pressure, and a flow selector valve for providing a fluid passageway between said liquid in said pressure regulator unit and said inlet side of a selected one of said check valves, whereby an operator can choose a desired liquid pressure for said syringe.

18. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues:

said flow limiting orifice having a diameter less than or equal to about 0.15 inches.

19. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet, said liquid inlet having a flow limiting orifice, said pressure relief outlet being in fluid communication with said supply chamber and adapted to release liquid from said pressure regulator unit, said pressure relief outlet having a check valve which opens to allow liquid to flow from said pressure relief outlet when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues;

a reservoir chamber in fluid communication with said supply chamber;

said supply chamber and said reservoir chamber being defined by inner and outer concentric tubes having a space therebetween, said inner concentric tube having an internal volume defining said supply chamber, said space between said inner and outer concentric tubes comprising an annular volume defining a reservoir chamber having said liquid outlet.

20. An irrigation syringe, comprising:

a handpiece;

a pressure regulator unit including a supply chamber having a liquid inlet having a flow limiting orifice opening to said supply chamber, a liquid outlet in fluid communication with said supply chamber and adapted to supply liquid to said handpiece, and a pressure relief outlet in fluid communication with said supply chamber and adapted to release liquid from said pressure regulator unit, said pressure relief outlet including a check valve which opens to allow liquid to flow therefrom when pressure in said supply chamber exceeds a predetermined value;

said check valve having a first flow area, said flow limiting orifice having a second flow area which is less than said first flow area of said check valve such that said pressure regulator unit provides a generally steady flow of pressure regulated liquid from said liquid outlet;

said handpiece having a liquid inlet in fluid communication with said liquid outlet of said pressure regulator unit, and a discharge opening from which pressure regulated liquid from said liquid inlet of said handpiece issues; and at least one temperature indicator on said syringe to indicate the temperature of liquid within said syringe.

21. The syringe of claim 20, wherein said handpiece further includes a manually operable valve in fluid communication with said liquid inlet and said discharge opening of said handpiece for controlling the flow of liquid from said discharge opening.

22. The syringe of claim 20 wherein said second flow area of said flow limiting orifice is less than one-half of said first flow area of said check valve.

23. The syringe of claim 20, wherein said temperature indicator is on said handpiece.

24. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet in fluid communication with said supply chamber and adapted to release liquid from said pressure regulator unit, said pressure relief outlet including a check valve which opens to allow liquid to flow therefrom when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues; and at least one temperature indicator on said syringe to indicate the temperature of liquid within said syringe;

said pressure regulator unit further including a reservoir chamber in fluid communication with said supply chamber, and a flow restrictive fluid connection providing said fluid communication between said supply and said reservoir chambers; said liquid outlet connected to said reservoir chamber.

25. The syringe of claim 24, wherein said pressure regulator unit further includes a pressure indicator mounted thereon for indicating the pressure of liquid in said pressure regulator unit.

26. The syringe of claim 25 including a second pressure indicator in said handpiece.

27. The syringe of claim 25, wherein said pressure indicator includes a cylinder and a spring-loaded piston movable within said cylinder in response to a change in pressure in said pressure regulator unit, said cylinder being separated from said liquid contained in said pressure regulator unit by an elastic, fluid-impermeable diaphragm, the pressure in said pressure regulator unit being indicated by the position of said spring-loaded piston in said cylinder.

28. The syringe of claim 25, including a first temperature indicator on said pressure regulator unit and a second temperature indicator on said handpiece.

29. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet in fluid communication with said supply chamber and adapted to release liquid from said pressure regulator unit, said pressure relief outlet including a check valve which opens to allow liquid to flow therefrom when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues; and at least one temperature indicator on said syringe to indicate the temperature of liquid within said syringe, said temperature indicator being on said pressure regulator unit.

30. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet in fluid communication with said supply chamber and adapted to release liquid from said pressure regulator unit, said pressure relief outlet including a check valve which opens to allow liquid to flow therefrom when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues;

at least one temperature indicator on said syringe to indicate the temperature of liquid within said syringe; and a pressure indicator on at least one of said pressure regulator unit and said handpiece for indicating the pressure of liquid in said syringe.

31. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet in fluid communication with said supply chamber and adapted to release liquid from said pressure regulator unit, said pressure relief outlet including a check valve which opens to allow liquid to flow therefrom when pressure in said supply chamber exceeds a predetermine value;

said handpiece having a liquid inlet in fluid communication with said liquid outlet of said pressure regulator unit, and a discharge opening from which pressure regulated liquid from said liquid inlet of said handpiece issues; and at least one pressure indicator on said syringe to indicate the pressure of water in said syringe.

32. The syringe of claim 31, including at least one temperature indicator on said syringe to indicate the temperature of water in said syringe.

33. The syringe of claim 32, wherein said pressure indicator is on one of said regulator unit and said handpiece.

34. The syringe of claim 33, wherein said temperature indicator is on one of said regulator unit and said handpiece.

35. The syringe of claim 31, wherein said liquid inlet to said pressure regulator unit includes a flow limiting orifice.

36. An irrigation syringe, comprising:

a handpiece;

a pressure regulator unit including a supply chamber having a liquid inlet, a liquid outlet in fluid communication with said supply chamber and adapted to supply liquid to said handpiece, and a pressure relief outlet in fluid communication with said supply chamber and adapted to release liquid from said pressure regulator unit, said pressure relief outlet including a check valve which opens to allow liquid to flow therefrom when pressure in said supply chamber exceeds a predetermined value;

said handpiece having a liquid inlet in fluid communication with said liquid outlet of said pressure regulator unit, and a discharge opening from which pressure regulated liquid from said liquid inlet of said handpiece issues; and at least one temperature indicator on said syringe to indicate the temperature of liquid within said syringe;

said pressure regulator unit further including a reservoir chamber in fluid communication with said supply chamber, said supply chamber and said reservoir chamber being defined by a pair of inner and outer concentric tubes having a space therebetween, said inner concentric tube having an internal volume defining said supply chamber, said space between said inner and outer concentric tubes comprising an annular volume defining a reservoir chamber having said liquid outlet.

* * * * *

UNITED STATES PATENT AND TRADEMARK OFFICE
CERTIFICATE OF CORRECTION

PATENT NO. : 5,685,851  
DATED : November 11, 1997  
INVENTOR(S) : Murphy et al.

It is certified that error appears in the above-identified patent and that said Letters Patent is hereby corrected as shown below:

Column 15,  
Line 58, after "issues" delete ":" and insert therefor -- ; --

Signed and Sealed this

Eleventh Day of February, 2003

JAMES E. ROGAN  
*Director of the United States Patent and Trademark Office*